United States Patent [19]

Schneider et al.

[11] Patent Number: 5,206,203
[45] Date of Patent: Apr. 27, 1993

[54] ACID-RESISTANT COPPER OXIDE-CHROMIUM OXIDE CATALYST FOR THE HYDROGENATION OF FATTY ACIDS AND FATTY ESTERS

[75] Inventors: Michael Schneider, Ottobrunn-Riemerling; Gerd Maletz, Brückmühl; Karl Kochloefl, Brückmühl/Heufeld, all of Fed. Rep. of Germany

[73] Assignee: Sud-Chemie Aktiengesellschaft, Fed. Rep. of Germany

[21] Appl. No.: 795,491

[22] Filed: Nov. 21, 1991

[30] Foreign Application Priority Data

Nov. 27, 1990 [DE] Fed. Rep. of Germany ....... 4037731

[51] Int. Cl.$^5$ .................. B01J 21/06; B01J 23/10; B01J 23/26; B01J 23/72
[52] U.S. Cl. .................... 502/304; 502/303; 502/308; 502/318; 568/885
[58] Field of Search ............. 502/304, 308, 318, 303; 568/885

[56] References Cited

U.S. PATENT DOCUMENTS

| | | | |
|---|---|---|---|
| 3,756,964 | 9/1973 | Frazee et al. | 252/454 |
| 3,767,595 | 10/1973 | Montgomery | 252/454 |
| 3,789,022 | 1/1974 | Schenker et al. | 252/462 |
| 3,855,388 | 12/1974 | Rosinski | 252/465 |
| 3,870,658 | 3/1975 | Farrauto et al. | 252/465 |
| 4,666,879 | 5/1987 | Kelly et al. | 502/244 |
| 5,030,609 | 7/1991 | Turner et al. | 502/318 |

FOREIGN PATENT DOCUMENTS

| | | | |
|---|---|---|---|
| 210795 | 4/1986 | European Pat. Off. | |
| 598633 | 3/1978 | U.S.S.R. | 502/318 |
| 1422476 | 1/1976 | United Kingdom | |

*Primary Examiner*—W. J. Shine
*Attorney, Agent, or Firm*—Herbert P. Price

[57] ABSTRACT

Acid-resistant copper oxide-chromium oxide catalysts for hydrogenation of fatty acids or fatty acid mixtures and/or the esters thereof are obtained through heat treatment of copper oxide and chromium oxide or of precursor compounds that are convertible into copper oxide or chromium oxide and which contain aluminum zirconium, cerium and/or lanthanum oxide as an additional metal component. The acid resistance is defined by the fact that the amount of copper which is dissolved by stirring 10 g of the catalyst for 2 minutes in 100 ml of 10 weight percent acetic acid at 20° C., is a maximum of 200 mg.

7 Claims, No Drawings

ACID-RESISTANT COPPER OXIDE-CHROMIUM OXIDE CATALYST FOR THE HYDROGENATION OF FATTY ACIDS AND FATTY ESTERS

BACKGROUND OF THE INVENTION

The field of art to which this invention is directed is hydrogenation catalysts.

Fatty alcohols, i.e., aliphatic, predominantly linear primary alcohols with chain lengths greater than eight carbon atoms represent especially significant intermediate products in the chemical industry. One of their primary uses is in the production of surfactants, such as fatty alkyl sulfates, polyglycol ethers or polyglycol ether sulfates.

The most important raw materials for the production of these alcohols are fatty acids, or fatty acid esters, in the form of mixtures of various chain lengths, which can be obtained for instance, from natural fats and oils. Conversion into fatty alcohols occurs through catalytic hydrogenation under pressure, for which catalysts based on copper-chromium have proven to be particularly effective.

The hydrogenation reaction is conducted as suspension hydrogenation, as vapor-phase hydrogenation, or in the trickle phase. Sufficiently high reaction rates are only achieved at pressures above 250 bar and temperatures in the 260° to 300° C. range. As a rule, the triglycerides are transesterified with methanol according to known methods before hydrogenation, the free fatty acids being esterified. Nevertheless, the reaction mixture contains a residual concentration of free carboxylic acids.

An important technical embodiment is represented by the suspension hydrogenation of fatty acids according to the LURGI process. In this process, the fatty acid mixture is continuously fed to the hydrogenation reactor and esterified in situ by the excess fatty alcohol present.

The presence of the free fatty acids obviously makes great demands on the acid resistance of the catalysts that are used. The catalyst metals—copper, in particular—can be eluted due to the attack of the acids, so that the catalyst's efficacy is impaired. Moreover, this also leads to contamination of the product.

A possible means of reducing the acid solubility of copper-chromium catalysts, is extraction with acetic acid. However, not only is this process particularly expensive, but the hydrogenation activity of the resulting catalyst is significantly reduced, which is not surprising, given the loss of active copper metal through the treatment with acetic acid.

It is further known that the crystallinity of copper-chromium catalysts can be increased through calcination at comparatively high temperatures, whereas the phases present are completely or partially converted into $CuCr_2O_4$ that has spinel structure depending on the copper-chromium molar ratio. As a result of this heat treatment, on the one hand the solubility in acid of the catalyst metals decreases, but on the other hand the inner surface of the catalyst, as determined by the BET method, is reduced. At the same time a drastic reduction in hydrogenation activity is observed.

Copper oxide-chromium oxide catalysts have also been used in other areas of application. For instance, German Patent No. DE-B-23 19 551 describes catalysts for the detoxification of exhaust gases, in particular from automobile engines, that contain aluminum, chromium, and copper oxide as substantial components. These catalysts are produced through mixing of an aluminum oxyhalide sol and a chromium oxyhalide sol, calcination of the mixture and impregnation of the calcinated product with a compound that supplies copper oxide. The catalyst need not be acid-resistant for the purpose indicated.

Copper chromite catalysts for the oxidation of the oxidizable hydrocarbons and carbon monoxide present in the exhaust gases of internal combustion engines are further known from U.S. Pat. No. 3,855,388 (German Patent Application No. DE-A-22 00 460). These catalysts are produced by mixing an aluminum oxide supporting material, of which at least 20 percent is present in hydrogenated condition, with copper chromite and then drying the product obtained in order to remove the water. These catalysts also need not be acid-resistant for the purpose indicated.

U.S. Pat. No. 3,870,658 similarly relates to copper chromite-aluminum oxide catalysts for the oxidation of carbon monoxide from automobile exhaust gases. The catalysts are obtained through the mixing of aqueous solutions of aluminum salts or aluminum oxide, copper salts, and chromium salts or chromium oxide, drying of the solutions and sintering of the product. Thereafter, the excess copper oxide is removed through treatment of the product with a strong mineral acid. As a result of this acid treatment, the catalysts obtained are probably acid-resistant; however, they do not have sufficient hydrogenation activity, since they do not contain promoting agents.

Copper chromite-aluminum oxide catalysts that can be used for hydrogenation reactions are further known from U.S. Pat. No. 3,756,964 (German Patent No. DE-B-23 11 114). A porous supporting material, such as aluminum oxide or silicic acid, is used to produce these catalysts, with copper oxide and chromium oxide precipitated in the pores of this supporting material. These oxides are converted into copper chromite through heating. Through this type of production, it is guaranteed that no copper or chromium compounds will enter the wash water when the catalyst is washed out. The catalysts, however, have insufficient hydrogenation activity.

Copper chromite catalysts that can be used as hydrogenation catalysts are further described in German Patent Application No. DE-A-22 46 382. These catalysts are produced by dissolving metallic copper in the presence of oxygen in an ammonium carbonate solution and mixing the tetraamine copper complex obtained with chromic acid or a solution of copper dichromate; thereafter, the basic copper ammonium chromate produced is calcinated in order to form a copper chromite catalyst. The copper chromite can also be precipitated on an inert supporting material, such as aluminum oxide. The activity of the catalysts obtained is, however, relatively small since the catalysts contain no promoters.

Copper chromite catalysts for the oxidation of hydrocarbons and carbon monoxide from the exhausts of combustion engines are also known from U.S. Pat. No. 3,789,022. In order to produce these catalysts, copper, cerium and chromium oxide layers are precipitated one after another on an aluminum oxide support. However, these catalysts have a low acid resistance.

Finally, a process in which catalysts based on copper oxide, which may contain chromium oxide, aluminum oxide and the oxides of lanthanoids among others, are used for the hydrogenation of carboxylic acid esters into alcohols is known from European Patent Application-A-0 210 795.

The objective of the present invention is to produce catalysts that combine significantly improved acid resistance with high activity in the hydrogenation of fatty acids or fatty acid mixtures and/or the esters thereof.

SUMMARY OF THE INVENTION

This invention is directed to copper oxide-chromium oxide hydrogenation catalysts. In one aspect, this invention related to copper oxide-chromium oxide catalysts which are acid resistant and have a high degree of hydrogenation activity. In another aspect, this invention pertains to a process for hydrogenating fatty acids or fatty acid esters or mixtures thereof using copper oxide-chromium oxide catalysts.

The acid-resistant catalysts of this invention contain (in analytical terms) about 20 to about 70 weight percent copper oxide (CuO), about 20 to about 70 weight percent chromium oxide ($Cr_2O_3$), and about 0.5 to about 25 weight percent, as an additional component, metal oxides selected from aluminum oxide ($Al_2O_3$), zirconium oxide ($ZrO_2$), cerium oxide ($Ce_2O_3$) or lanthanum oxide ($La_2O_3$) or mixtures thereof. The catalysts, after the thermal treatment of the metal oxides or precursor compounds convertible into the oxides (usually at a temperature of about 300° C. to about 900° C.) have a surface area determined by the BET method, of at least about 8 $m^2/g$. The acid resistance of the catalyst, as determined by measuring the solubility of the copper in the catalyst when 10 grams of the catalyst are stirred for 2 minutes in 10 percent acetic acid in water at 20° C., is a maximum of 200 mg.

The catalyst of this invention preferably contains (in analytical terms) about 30 to about 55 weight percent CuO, about 30 to about 55 weight percent $Cr_2O_3$ and about 1 to about 15 weight percent additional metal oxide component. The additional metal oxide components are preferably $ZrO_2$ or $Ce_2O_3$.

DESCRIPTION OF THE INVENTION

The copper oxide-chromium oxide catalysts of this invention are prepared according to relatively well-known methods. For instance, solutions of copper nitrate and ammonium chromate can be precipitated as a copper ammonium chromate complex, followed by the addition of a compound of one or more of the metal modifiers. Suitable compounds are the metal oxides or precursor compounds which are converted into oxides by thermal decomposition. Precursor compounds are, for example, nitrates, sulfates, or carbonates.

Heat treatment is necessary in order to convert the copper-chromate-containing precipitation products into the form according to the invention. This calcination can be conducted at temperatures between about 300° and about 900° C., preferably at temperatures between about 500° and 750° C. The calcination is conducted statically, e.g., in suitable tray furnaces, as well as continuously, e.g. in rotary kilns. The necessary residence time is to be determined experimentally for the particular calcination unit used. The inner surface of the calcinated product, which is to be determined according to the BET method, is the criterion for this. It should be between about 8 $m^2/g$ and about 60 $m^2/g$, preferably between about 10 $m^2/g$ and about 40 $m^2/g$.

The catalysts of this invention are used for the liquid-phase hydrogenation of fatty acids or fatty acid mixtures with 5 to 24 carbon atoms and/or the esters thereof, in certain cases in admixture with alcohols, into the corresponding fatty alcohols.

The fatty acids or fatty acid mixtures are preferably esterified in situ by the alcohol present in the reaction mixture. Preferably, the alcohols present in the reaction mixture will represent fatty alcohols or mixtures of fatty alcohols with 4 to 24 carbon atoms.

The following examples explain the production of copper-chromium catalysts according to the invention and their use for the suspension hydrogenation of fatty acids.

EXAMPLE 1

800 g of chromic acid are dissolved in 1000 ml of deionized water, 1660 g of 25 percent ammonia are added and the mixture is diluted to a total volume of 8000 ml. 150 g of zirconium nitrate solution, containing 30 g of $ZrO_2$, and copper nitrate, containing 447 g of copper, are dissolved to a total volume of 5000 ml. Precipitation is carried out through admixture of the nitrate solution to the ammonium chromate solution at 60° C.

The filter cake is filtered and calcinated as follows: it is heated to a temperature of 320° C. at a heating rate of 2°/min and maintained at this temperature for one hour; the temperature is then increased to 600° C. at 2°/min and this temperature is then maintained for 3 hours.

The catalyst obtained in this way contains 2.5 percent $ZrO_2$; the BET surface is 21 $m^2/g$.

COMPARATIVE EXAMPLE A

A catalyst is prepared using the procedure described in Example 1 except no zirconium nitrate is added to the copper nitrate solution. This example does not, therefore, involve a catalyst according to the invention. The BET surface of the catalyst is 4 $m^2/g$.

COMPARATIVE EXAMPLE B

This catalyst is prepared as described in Example A except calcination is conducted in the following way: heating to 320° C. at 2°/min, maintenance at this temperature for one hour, heating to 370° C. and maintenance at this temperature for 3 hours. The BET surface is 30 $m^2/g$.

EXAMPLES 2 TO 4

Using the procedure described in Example 1, additional copper-chromium oxide catalysts are produced, but with replacement of the zirconium nitrate used therein with the additives listed below. If the pH falls below 6.2 during precipitation, concentrated ammonia is added; the final pH is 6.8. The BET surfaces of the catalysts are also listed for the purpose of comparison.

| Example | Additive | Original Weight | BET surface |
| --- | --- | --- | --- |
| 2 | $Al(NO_3)_3 \times 9 H_2O$ | 1000 g | 46 $m^2/g$ |
| 3 | $Ce(NO_3)_3 \times 6 H_2O$ | 342 g | 16 $m^2/g$ |
| 4 | $La(NO_3)_3 \times 6 H_2O$ | 361 g | 21 $m^2/g$ |

The following test serves to determine the relative resistance to acid attack: 10 g of the catalyst are stirred for 2 min at 20° C. in 100 ml of 10 percent acetic acid. The extracted copper in relation to the catalyst amount used is then determined.

The hydrogenation activity of the catalysts in the suspension hydrogenation of fatty acids was determined in the following way:

A 500 ml agitated autoclave is filled with 3 g of catalyst and 180 g of a commercial fatty alcohol mixture (CONDEA Alfol 1218). After activation of the catalyst at a temperature of 200° C. and a hydrogen pressure of 300 bar, the temperature is raised to 300° C.; then 20 g of lauric acid are added. During the course of the reaction, samples for the determination of the saponification value are taken from the reaction mixture. The degree of conversion can be defined at $$U = 1 - (VZ_t/VZ_o)$$

with t and o denoting the saponification values at a time t and at the outset of the reaction. Assuming first order kinetics the specific reaction velocity k and the half-value time $t_{\frac{1}{2}}$ can be expressed as $t_{\frac{1}{2}} = \ln 2/k$.

The following table summarizes the solubilities obtained for copper in the manner described above as a measure of the acid tolerance and the half-value times as a characteristic quantity for the hydrogenation activity. As a formal combination of these two criteria, a quality factor, equal to one thousand time the reciprocal of the product of the acid solubility and the half-value time was defined.

| Example | Acid solubility mg Cu/10 g cat. | Hydrogenation activity $t_{1/2}$ | Quality factor |
| --- | --- | --- | --- |
| A (comp.) | 90 | 20 | 0.56 |
| B (comp.) | 420 | 8.3 | 0.29 |
| 1 | 70 | 8.6 | 1.66 |
| 2 | 130 | 9.6 | 0.95 |
| 3 | 30 | 11.0 | 3.03 |
| 4 | 150 | 11.8 | 0.85 |

What is claimed is:

1. An acid-resistant catalyst for the hydrogenation of fatty acids or fatty acid esters or mixtures thereof which comprises (in analytical terms) about 20 to about 70 weight percent CuO, about 20 to about 70 weight percent $Cr_2O_3$ and about 0.5 to about 25 weight percent of additional metal oxide selected from zirconium, cerium, or lanthanum oxide or mixtures thereof, wherein said catalysts, after thermal treatment of the metal oxides or precursor compounds convertible into the oxides, has a specific surface area of about 8 $m^2/g$ to about 60 $m^2/g$ and wherein the acid resistance as measured by the solubility of the copper in the catalyst in acid is a maximum of 200 mg. as determined by stirring 10 grams of the catalyst in 10 weight percent aqueous acetic acid at 20° C. for 2 minutes.

2. The catalyst of claim 1 wherein the specific surface area is about 10 to about 40 $m^2/g$.

3. The catalyst of claim 1 which contains (in analytical terms) about 30 to about 55 weight percent CuO, about 30 to about 55 weight percent $Cr_2O_3$ and about 1 to about 15 weight percent zirconium, cerium, or lanthanum oxide or mixtures thereof.

4. The catalyst of claim 3 which contains (in analytical terms) CuO, $Cr_2O_3$ and $ZrO_2$.

5. The catalyst of claim 3 which contains (in analytical terms) CuO, $Cr_2O_3$ and $Ce_2O_3$.

6. The catalyst of claim 1 wherein the oxides or precursor compounds convertible into the oxides are heated at about 300° C. to about 900° C.

7. The catalyst of claim 1 wherein the oxides or precursor compounds convertible into the oxides are heated at about 500° C. to about 750° C.